United States Patent
Walsh

(10) Patent No.: US 10,842,948 B2
(45) Date of Patent: Nov. 24, 2020

(54) RETRACTABLE SYRINGE

(71) Applicant: Global Medisafe Holdings LTD, Newcastle (AU)

(72) Inventor: Allan Walsh, Medowie (AU)

(73) Assignee: GLOBAL MEDISAFE HOLDINGS LTD, Newcastle (AU)

( * ) Notice: Subject to any disclaimer, the term of this patent is extended or adjusted under 35 U.S.C. 154(b) by 113 days.

(21) Appl. No.: 15/773,905

(22) PCT Filed: Nov. 18, 2016

(86) PCT No.: PCT/AU2016/005119
§ 371 (c)(1),
(2) Date: May 4, 2018

(87) PCT Pub. No.: WO2017/079811
PCT Pub. Date: May 18, 2017

(65) Prior Publication Data
US 2018/0326160 A1   Nov. 15, 2018

(30) Foreign Application Priority Data

Nov. 10, 2015  (CN) .......................... 2015 1 0761492
Nov. 10, 2015  (CN) ..................... 2015 2 0893201 U

(51) Int. Cl.
*A61M 5/32*    (2006.01)
*A61M 5/50*    (2006.01)

(52) U.S. Cl.
CPC ........... *A61M 5/3234* (2013.01); *A61M 5/508* (2013.01); *A61M 2005/3236* (2013.01)

(58) Field of Classification Search
CPC ........ A61M 5/3234; A61M 2005/3236; A61M 5/508
See application file for complete search history.

(56) References Cited

U.S. PATENT DOCUMENTS

| 5,407,436 A | 4/1995 | Toft et al. | |
|---|---|---|---|
| 2003/0050601 A1* | 3/2003 | Righi | A61M 5/3234 604/110 |
| 2010/0076378 A1* | 3/2010 | Runfola | A61M 5/3234 604/110 |

FOREIGN PATENT DOCUMENTS

| WO | 0048651 A1 | 8/2000 |
|---|---|---|
| WO | 2006096901 A1 | 9/2006 |
| WO | 2006096909 A1 | 9/2006 |
| WO | 2008009063 A1 | 1/2008 |
| WO | 2008128274 A1 | 10/2008 |
| WO | 2013083979 A1 | 6/2013 |

OTHER PUBLICATIONS

International Search Report and Written Opinion dated Jan. 31, 2017 in International Application No. PCT/AU2016/051119, 13 pages.

* cited by examiner

*Primary Examiner* — Amber R Stiles
(74) *Attorney, Agent, or Firm* — Berg Hill Greenleaf Ruscitti LLP

(57) ABSTRACT

An auto-retractable syringe having a barrel and a plunger wherein engagement of said plunger with an otherwise immobilised needle hub allows a biasing member to push the needle hub into a cavity in the plunger.

9 Claims, 4 Drawing Sheets

RETRACTABLE SYRINGE

CROSS REFERENCE TO RELATED APPLICATIONS

This application is a national stage application under 35 U.S.C. 371 and claims the benefit of PCT Application No. PCT/AU2016/051119 having an international filing date of Nov. 18, 2016, which designated the United States, which PCT application claimed the benefit of Chinese Patent Application Nos. 201510761492 and 201520893201, filed Nov. 10, 2015, the disclosure of each of which are incorporated herein by reference.

TECHNICAL FIELD

The invention relates to the field of hypodermic syringe manufacture. In particular, the invention relates to a retractable safety syringe, in which the needle is capable of being withdrawn into the barrel of the syringe after use via a spring or similar mechanism.

BACKGROUND OF THE INVENTION

Safety syringes for hypodermic needles are becoming a very important tool of healthcare. The ability to prevent needle-stick injuries is extremely important in preventing the spread of blood-borne diseases.

One particular type of safety syringe is the retractable syringe. That is: a syringe wherein there is provided a mechanism, usually a spring, inside the syringe that is activated upon completion of the injection of the fluid, whereby the spring acts to retract the needle inside the syringe barrel. This prevents the needle from causing a needle-stick injury, and in particular it allows the needle operator to withdraw the needle via a one-handed operation, which makes it much easier to achieve in the situation of providing injections to patients in a busy hospital or clinic.

One type of retractable syringe is that disclosed in WO 2006/096901, wherein there is provided a syringe with a hollow plunger that can accommodate a withdrawn needle and needle hub, the hub and needle being actuated by the expansion of a spring into the plunger, and where the spring is released by pressure of the plunger on the assembly that holds the hub in place by restraining the spring from release.

Such syringes are referred to commonly as 'auto-retractable', meaning that the actuation of the needle retraction is provided by a mechanism in the syringe itself, as opposed to requiring the operator to pull, push or otherwise move the needle into the barrel of the syringe.

A drawback with this type of retractable syringe is that they are prone to liquid leakage, and the mechanism tends to suffer from functional reliability issues.

Other designs are relatively complex and so are difficult or expensive to manufacture. Yet other designs do not allow for full dispensing of the injectable fluid, due to dead-zones being left in the barrel.

Accordingly, it is an object of the invention to provide a retractable syringe construction that ameliorates at least some of the problems associated with the prior art.

SUMMARY OF THE INVENTION

According to a first aspect of the invention, there is provided an auto-retractable syringe having a barrel and a plunger moveable within said barrel, said barrel having a gland assembly inside a forepart thereof, said gland assembly housing removable a needle hub to which is attached a hypodermic needle; wherein a biasing member is disposed between the gland assembly and said needle hub so as to tend to urge the needle hub into said barrel; wherein said plunger has an internal cavity capable of receiving the needle hub; wherein the needle hub is kept in place prior to use by a detent arrangement that prevents movement of the hub both into and out of the barrel; wherein engagement of said plunger with said needle hub forces the detent arrangement to release, allowing the biasing member to push the needle hub into said cavity in the plunger.

This type of syringe represents an improvement over the prior art in that leakage of fluid is reduced or eliminated, and also the syringe is of simpler, and therefore of more economical constructions. The instantaneous retraction of the needle inside the barrel via the biasing member (e.g. a spring) means the syringe can be used and disabled in one action, and with a one-handed operation.

Preferably, the detent arrangement comprises one or more indent regions in the needle hub, said indent region or regions having a profile that, when engaged would prevent movement of said hub, whether into or out of the barrel; and a set of resilient claws (e.g. three claws) that have a complementary profile to that of the indent or indents, that occupies the indent regions, thereby to lock the needle hub in place and defeating the force of the biasing member. More preferably, the internal profile of said indent is square or rectangular. The detent arrangement that holds the needle hub more firmly in place, by disallowing movement in both directions, provides a particular advantage.

In a preferred embodiment, the upper region of said claws have an inclined surface that is inclined away from the needle hub, such that when engaged by a member moving in the direction of injection, the force applied thereby will tend to push the claws away from the needle hub, thereby releasing it and allowing the biasing member to push the hub into the plunger. Such upper surfaces allow for a more reliable engagement of the claws, and allow simple engagement by another moving part to create a controlled disengagement of the claws.

Preferably, the plunger has at its liquid-engaging end a stopper, said stopper being held in place by a detent arrangement that may be overcome by the force of the biasing member pushing the needle hub into the plunger. This allows the plunger to be pushed back into the cavity along with the needle. It also makes the syringe easier to manufacture and allows a more efficiently shaped plunger stopper to be employed, such as one with a partly-spherical liquid-engaging surface.

In a preferred embodiment, the biasing member is a spring, and said spring is installed partly compressed. Partial compression of the spring (as opposed to full compression) allows for simpler construction and better control of the retraction operation.

Now will be described, by way of a specific, non-limiting example, a preferred embodiment of the invention with reference to the drawings.

DETAILED DESCRIPTION OF THE INVENTION

The invention may be embodied by the arrangement of working parts at the 'dispensing' end of a retractable hypodermic syringe. These are best understood by reference to the accompanying figures.

Figure 1:
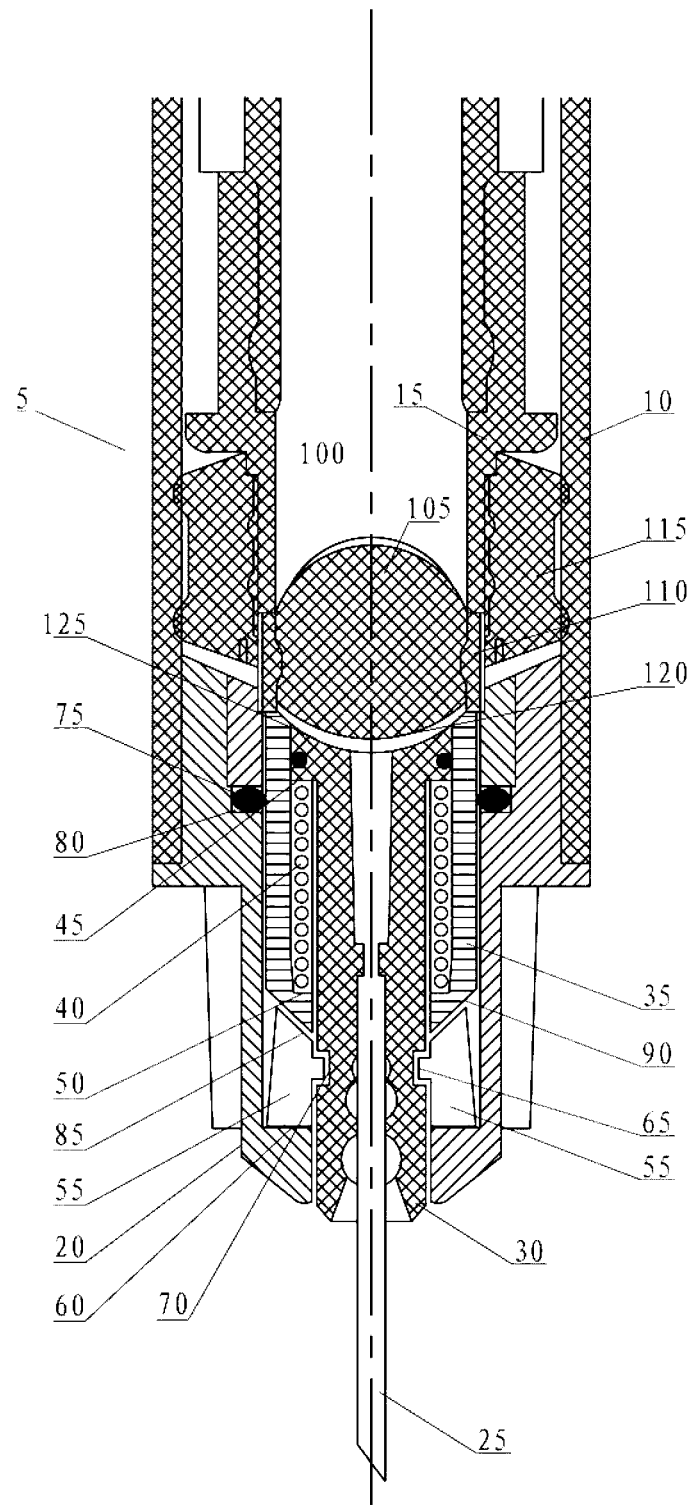
FIG. 1 is a cross-sectional view of the 'needle' end of a syringe according to the invention.

Turning to FIG. 1, there is shown an auto-retractable syringe 5. The major components of the syringe are the barrel 10, the plunger 15, the gland 20 and the needle 25. The gland 20 is inserted in the barrel 10 in a press-fit manner and houses the needle hub assembly. It is also possible for the gland to be a screw-in type.

The needle hub assembly includes the needle hub 30, in which is inserted the needle 25. A sliding activator sleeve 35 is fitted around the needle hub and in between these two parts is placed a partially compressed spring 40. The spring 40 is in contact with a stepped rear-facing surface 45 of the hub and an inner forward stepped surface 50 of the sleeve 35. Thus the spring's role is to tend to force the hub 30 rearward relative to the sleeve 35.

However, prior to dispensing, this tendency of the spring 40 is held in check by a detent mechanism. This mechanism consists of three resilient claws 55 that protrude from the inner front surface 60 of the gland 20. Each of said claws have a square or rectangular lug 65 oriented toward the needle hub 25. They also have an rearward 'head' surface 85 that is smooth but sloped in a sense that it is furthest from the surface of the hub 30 at its upper-most extremity, and said surface is closer to the hub 30 or the gland 20 at the 'dispending end' of the claw 55.

The activator sleeve 35 is chamfered around its forward edge to produce an angled surface 90. In assembly, this chamfered surface 90 is located as close as possible to the complementarily sloped 'head' surface 85 of the three claws 55. The closeness of the location means a more rapid response to dispensing pressure on the activation sleeve 35, as there is less distance to travel.

The needle hub 25 has a complementary groove 70 around its circumference that is located such that the lugs 65 are received within said groove 70 in pre-dispensing configuration. The positioning and shape of the lugs 65 and the groove 70 provide a very reliably immobile positioning of the needle hub, as the square shape of the lugs/groove combination prevents movement of the hub 30 in either a forward or rearward direction.

An O-ring 75 is located around the outer circumference of the activator sleeve 35 and positioned in an internal groove 80 in the inner surface of the gland 20. This provides a more effective seal around the hub/sleeve assembly to prevent fluid leakage during dispensing.

The plunger 15 is formed as a hollow barrel, with an internal cavity 100. The end of said plunger barrel is sealed via a stopper 105 made of rubber and which is held in place by a simple detent ring 110. On the outside of the plunger barrel is arranged a rubber gasket 115, which makes a sealing engagement with the inner surface of the barrel 10. The forward surface 120 of the stopper is partly spherical and the rear surface 125 of the needle hub 30 are shaped in a complementary manner to afford maximum dispensing and minimal 'dead zones'.

Figure 2:
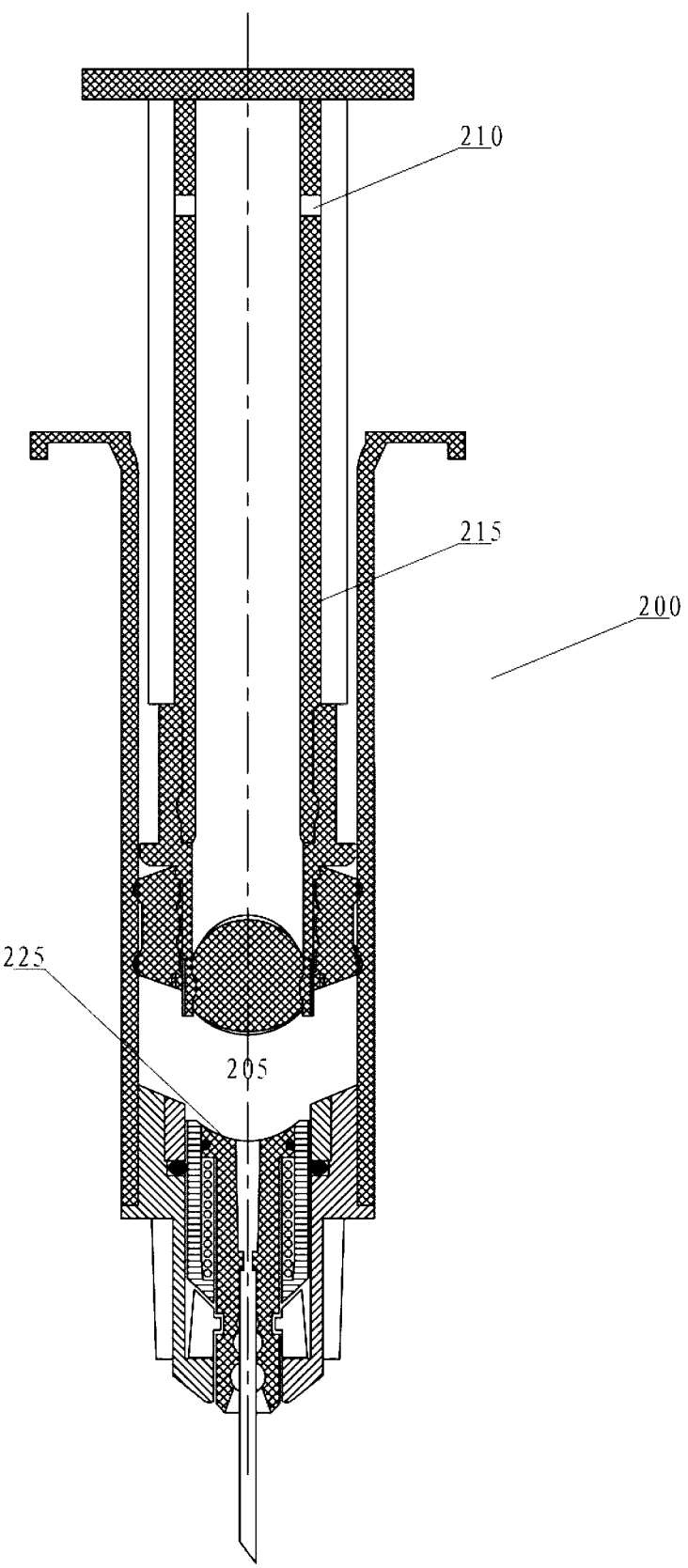
FIG. 2 is a cross-sectional view of a syringe according to the invention, shown prior to completion of dispensing.

Turning to FIG. 2, there is shown a syringe 200 according to the invention during the fluid dispensing phase, where the fluid is in the cavity 205 formed between the plunger 215 and the rear of the needle hub 225. The remainder of the parts are as described in FIG. 1. In addition, it will be noted that there are provided 'air escape' holes 210 in the plunger barrel 215, which are required to allow air to escape as the hub is (later) pushed in to the cavity 205.

Figure 3:
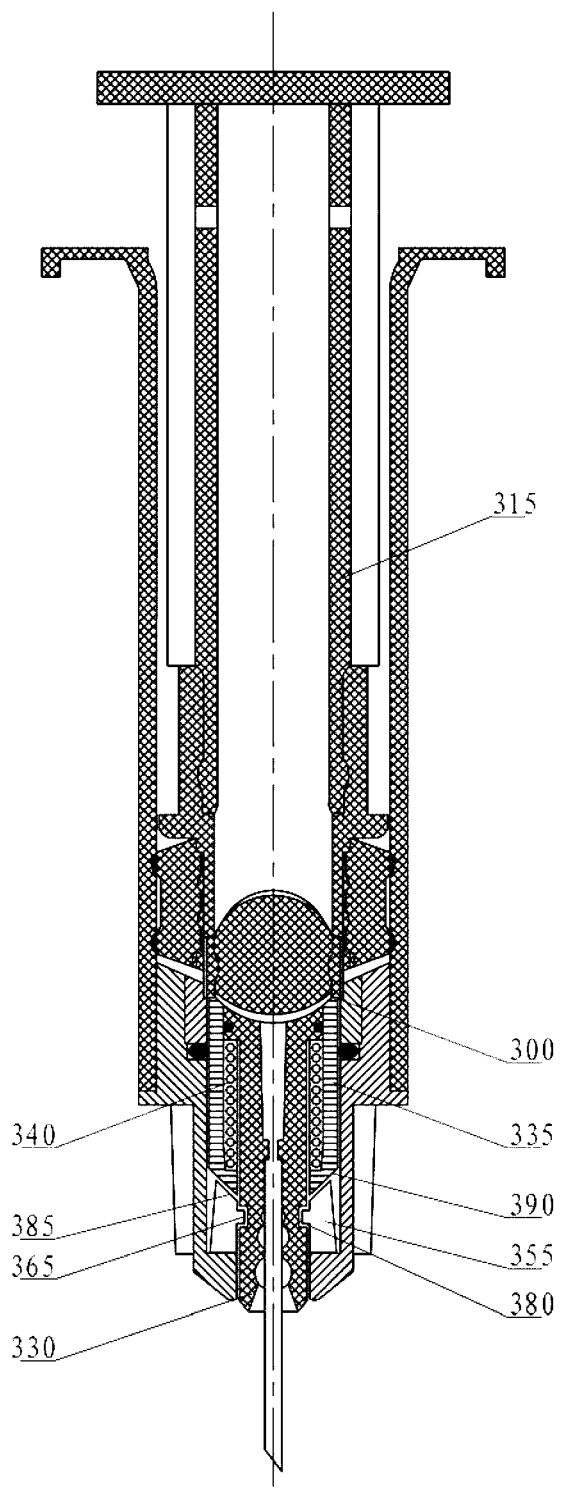
FIG. 3 is a cross-sectional view of the syringe of FIG. 4, shown at the point of completion of dispensing.

Turning to FIG. 3, there is shown the syringe of FIG. 2 at the point of full dispensing, just as pressure is brought to bear on the rear end 300 of the activation sleeve 335 by the plunger 315. As the activation sleeve 335 is pushed forward, the chamfered forward surface 390 can be seen making contact with the angled 'head' surface 385 of the claws 355 and beginning to force the claws away from the hub 330, thereby causing the lugs 365 to begin to disengage with the groove 380, thereby to release the spring 340.

Figure 4:
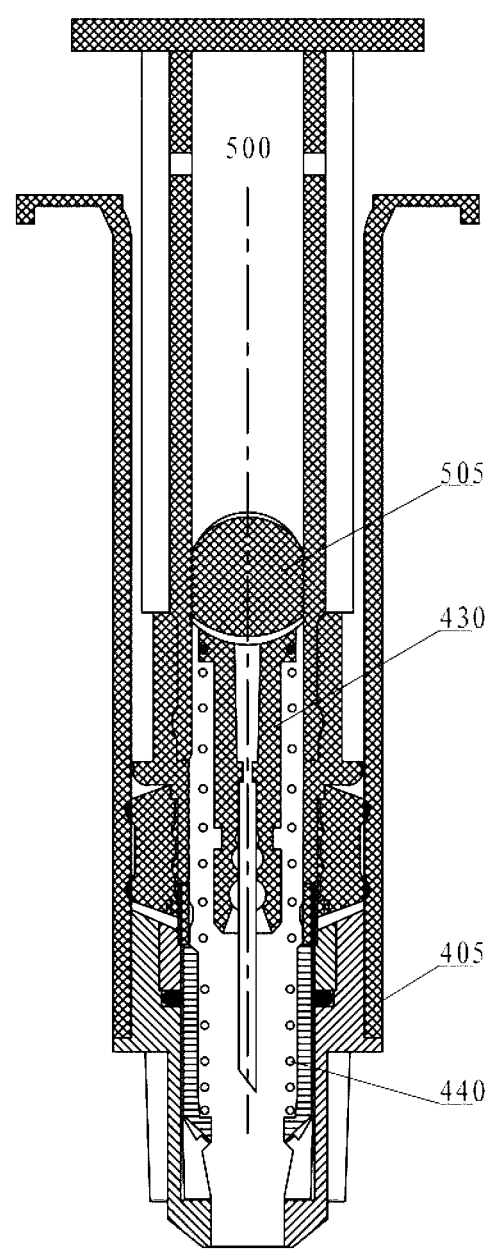
FIG. 4 is a cross-sectional view of the syringe of FIG. 4, shown following retraction of the needle hub.

Turning to FIG. 4, there is shown the syringe of FIG. 3 post the release of the detent mechanism. The spring 440 has extended and thereby pushed the needle hub 430 and the stopper 505 well inside the plunger's internal cavity 500. The needle 425 can be seen to be also well inside the body of the syringe 405. At his point the syringe can be safely disposed of without risk of needle-stick injury.

It will be appreciated by those skilled in the art that the above described embodiment is merely one example of how the inventive concept can be implemented. It will be understood that other embodiments may be conceived that, while differing in their detail, nevertheless fall within the same inventive concept and represent the same invention.

The invention claimed is:

1. An auto-retractable syringe having a barrel and a plunger moveable within said barrel, said barrel having a gland assembly inside a forepart thereof, said gland assembly removably housing a needle hub to which is attached a hypodermic needle; wherein a compressed spring is disposed between the gland assembly and said needle hub so as to tend to urge the needle hub into said barrel; wherein said plunger has an internal cavity capable of receiving the needle hub and one or more holes to allow displaced air to escape; wherein the needle hub is kept in place prior to use by a detent arrangement that prevents movement of the needle hub both into and out of the barrel; wherein said detent arrangement comprises one or more square or rectangular indent regions in the needle hub, said indent region or regions having a profile that, when engaged prevent movement of said needle hub, whether into or out of the barrel; and a set of resilient claws that have complementary square or rectangular lugs that occupy the indent regions, thereby to lock the needle hub in place and to resist the release of said compressed spring; said gland assembly incorporating a sliding activation sleeve fitted around the needle hub and said compressed spring; said spring being in contact with the needle hub and said sliding activation sleeve, wherein engagement of said plunger with said sliding activation sleeve forces the detent arrangement to release, allowing the compression spring to push the needle hub into said cavity in the plunger.

2. The syringe of claim 1, wherein the upper region of said claws have an inclined surface that is inclined away from the needle hub, and said sliding activation sleeve is chamfered around its forward edge to produce an angled surface; and wherein in assembly, this chamfered surface is located as close as possible to the complementarily inclined surface of said claws, such that when said sliding activation sleeve is engaged by said plunger moving in the direction of injection, the force applied thereby will tend to push the claws away from the needle hub, thereby releasing it and allowing the compression spring to push the needle hub into the plunger.

3. The syringe of claim 2, wherein the plunger has at its liquid-engaging end a stopper, said stopper being held in place by a detent arrangement that may be overcome by the force of the compression spring pushing the needle hub into the plunger.

4. The syringe of claim 3, wherein the stopper has a partly-spherical liquid-engaging surface.

5. The syringe of claim 4, wherein said compression spring is installed partly compressed.

6. The syringe of claim 3, wherein said compression spring is installed partly compressed.

7. The syringe of claim 2, wherein said compression spring is installed partly compressed.

8. The syringe of claim 1, wherein the plunger has at its liquid-engaging end a stopper, said stopper being held in place by a detent arrangement that may be overcome by the force of the compression spring pushing the needle hub into the plunger.

9. The syringe of claim 1, wherein said compression spring is installed partly compressed.

* * * * *